(12) United States Patent
Kim et al.

(10) Patent No.: US 10,196,379 B2
(45) Date of Patent: Feb. 5, 2019

(54) VIOLOGEN COMPOUND, AND ELECTROLYTE, LIGHT-TRANSMITTANCE-VARIABLE PANEL AND DISPLAY DEVICE INCLUDING THE VIOLOGEN COMPOUND

(71) Applicant: LG DISPLAY CO., LTD., Seoul (KR)

(72) Inventors: June-Hwan Kim, Seoul (KR);
Seong-Yong Uhm, Goyang-si (KR);
Seok-Ho Lee, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 0 days.

(21) Appl. No.: 15/827,868

(22) Filed: Nov. 30, 2017

(65) Prior Publication Data

US 2018/0155321 A1   Jun. 7, 2018

(30) Foreign Application Priority Data

Dec. 7, 2016   (KR) .......................... 10-2016-0165613

(51) Int. Cl.
*G02F 1/15*      (2006.01)
*C07D 401/14*    (2006.01)
*C09K 9/02*      (2006.01)

(52) U.S. Cl.
CPC ............ *C07D 401/14* (2013.01); *C09K 9/02* (2013.01); *G02F 1/1521* (2013.01); *C09K 2211/1077* (2013.01)

(58) Field of Classification Search
CPC ................ C07D 401/14; C09K 9/02; C09K 2211/1077; G02F 1/1521
See application file for complete search history.

(56) References Cited

U.S. PATENT DOCUMENTS 9,964,828 B2 *   5/2018   Theiste ................. G02F 1/1506
2006/0007519 A1   1/2006   Kanouni et al.

FOREIGN PATENT DOCUMENTS

| JP | 2001-21926 A | 1/2001 |
| KR | 2010-0027510 A | 3/2010 |
| KR | 10-1162556 B1 | 7/2012 |
| KR | 101535100 B1 | 7/2015 |
| KR | 10-2016-0083236 A | 7/2016 |

* cited by examiner

*Primary Examiner* — Joseph P Martinez
(74) *Attorney, Agent, or Firm* — Birch, Stewart, Kolasch & Birch, LLP

(57) ABSTRACT

A display device comprises a light-transmittance-variable panel including a first substrate and a second substrate facing each other; a first transparent electrode on the first substrate; a second transparent electrode on the second substrate; and an electrochromic layer between the first transparent electrode and the second transparent electrode and containing a viologen compound; and a display panel on one side of the light-transmittance-variable panel and including a plurality of display units and a plurality of transparent units.

11 Claims, 6 Drawing Sheets

VIOLOGEN COMPOUND, AND ELECTROLYTE, LIGHT-TRANSMITTANCE-VARIABLE PANEL AND DISPLAY DEVICE INCLUDING THE VIOLOGEN COMPOUND

CROSS-REFERENCE TO RELATED APPLICATIONS

This application claims the priority benefit under 35 U.S.C. § 119(a) of Korean Patent Application No. 10-2016-0165613, filed on Dec. 7, 2016, in the Korean Intellectual Property Office, which is incorporated herein by reference into the present application.

BACKGROUND

Field of the Disclosure

The present disclosure relates to a compound capable of exhibiting electrochromism. More particularly, the present disclosure relates to a viologen compound exhibiting excellent electrochromic and excellent light-resistance characteristics; an electrolyte; a light-transmittance-variable panel; and a display device that includes the viologen compound.

Discussion of the Related Art

As our information society has evolved, there has been a growing interest in various flat-panel display devices, which can produce excellent images. Among such flat-panel display devices, liquid-crystal display (LCD) devices and organic light-emitting diode (OLED) display devices have been widely used.

The LCD device displays an image using the optical anisotropy and polarization properties of a liquid-crystal molecule. For example, in an LCD device, data electrodes and common electrodes are alternately disposed on a first substrate, and a liquid-crystal layer containing a liquid-crystal molecule is interposed between the first substrate and a second substrate, in which case the first substrate and second substrate face each other. Meanwhile, the OLED display device emits light by using an organic light-emitting layer between an anode and a cathode. The combination of a hole injected from the anode with an electron injected from the cathode in the organic light-emitting layer leads to an exciton, and light is generated as excitons fall from an excited state to the ground state.

Recently, there has been a growing interest in transparent display devices having a transparent front surface to allow light transmission. The transparent display device has been attracting particular attention as a window-type display device for so-called smart windows. However, since the transparent display device does not have a black color state, it has a low contrast ratio and poor image visibility. To solve this problem, a method of disposing, on one surface of a display panel, a light-shielding plate whose light transmittance can be changed through the color change or migration of particles has been proposed. A liquid-crystal panel, an electrophoretic panel, an electrowetting panel, an electrochromic panel, or the like with variable light transmittance has been used as the light-shielding plate.

A liquid-crystal panel used as a light-transmittance-variable panel has a low light transmittance in a light-transmitting mode due to an interposed liquid-crystal layer included therein. Also, when color filters are employed to implement a variety of colors, low luminance may result, and a low contrast ratio may be attained due to the poor light-shielding efficiency of the color filters.

The electrophoretic panel is based on electrophoresis in which the migration of charged particles is affected by whether or not a voltage is applied. Generally, when a voltage is applied to an electrophoretic panel, black charged particles are driven to migrate towards a transparent electrode and block light transmission, and when an opposite voltage is applied, white charged particles are driven to migrate towards the transparent electrode and transmit or reflect light. Accordingly, the electrophoretic panel is in a light-transmitting mode when no voltage is applied, and a light-shielding mode when a voltage is applied.

However, in the electrophoretic panel, it is difficult to disperse black electrophoretic particles and/or white electrophoretic particles uniformly throughout the electrolyte layer. In addition, when a fluid is used as an electrolyte, that is, a medium through which electrophoretic particles migrate, the electrophoretic particles and electrolyte may leak to the outside.

When an electrowetting-type light-transmittance-variable panel is used, the manufacture of such a panel by using a black oil is not easy, and problems such as precipitation of a black dye or pigment and leakage of a fluid such as an oil used to implement color may occur.

Meanwhile, the electrochromic panel utilizes an electrochromic material whose color may reversibly change as a result of an oxidation-reduction reaction affected by whether or not electrical power is applied. In this case, an electrolyte is used to cause a color change of the electrochromic material. For example, Korean Laid-open Patent Application No. 2010-0027510 discloses an electrochromic device employing an organic electrochromic material and a liquid electrolyte. However, when only an organic electrochromic material is used along with a liquid electrolyte, a poor light-shielding ability is attained due to limited solubility of the material in the liquid electrolyte. Also, since it is difficult for the organic electrochromic material to form a layer on its own, the material is dissolved in a liquid electrolyte for use; however, in this case, a problem of fluid leakage may still occur. In particular, the electrolyte currently being used in light-transmittance-variable panels has poor light-resistance characteristics such that performance characteristics, particularly light-shielding characteristics, thereof significantly degrade with time.

SUMMARY

Accordingly, embodiments of the present disclosure are directed to a viologen compound; an electrolyte; a light-transmittance-variable panel; and a display device including the viologen compound that substantially obviate one or more of the problems due to limitations and disadvantages of the related art. An object of the present disclosure is directed to provide a viologen compound exhibiting excellent performance characteristics and excellent light-shielding characteristics; an electrolyte; a light-transmittance-variable panel; and a display device that includes the viologen compound.

To achieve these and other advantages and in accordance with the purpose of the present disclosure, as embodied and broadly described herein, there is provided a viologen compound in which piperidine moieties are linked, by a linker, to either side of a bipyridinium-salt moiety.

The viologen compound is represented by Chemical Formula 1 provided below:

Chemical Formula 1

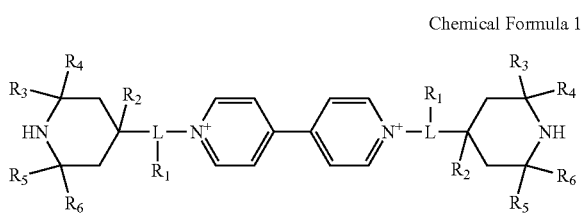

In Chemical Formula 1, $R_1$ is hydrogen, deuterium, tritium, or a linear or branched C1-C20 alkyl group; $R_2$ is hydrogen, deuterium, tritium, a C5-C30 aryl group, or a C4-C30 heteroaryl group; $R_3$ to $R_6$ are each independently hydrogen, deuterium, tritium, or a linear or branched C1-C10 alkyl group; and L is a C3-C10 alkylene group that is unsubstituted or substituted by an oxo group (=O).

Another aspect of the present disclosure is to provide an electrolyte containing the viologen compound represented by Chemical Formula 1.

Another aspect of the present disclosure is to provide a light-transmittance-variable panel including a first substrate and a second substrate facing each other; a first transparent electrode on the first substrate; a second transparent electrode on the second substrate; and an electrochromic layer between the first transparent electrode and the second transparent electrode and containing the viologen compound represented by Chemical Formula 1.

Another aspect of the present disclosure is to provide a display device comprising: a light-transmittance-variable panel including a first substrate and a second substrate facing each other; a first transparent electrode on the first substrate; a second transparent electrode on the second substrate; and an electrochromic layer between the first transparent electrode and the second transparent electrode and containing the viologen compound represented by Chemical Formula 1; and a display panel on one side of the light-transmittance-variable panel and including a plurality of display units and a plurality of transparent units.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and which are incorporated in and constitute a part of this specification, illustrate embodiments of the invention and together with the description serve to explain the principles of the invention. In the drawings.

DETAILED DESCRIPTION

Figure 1:
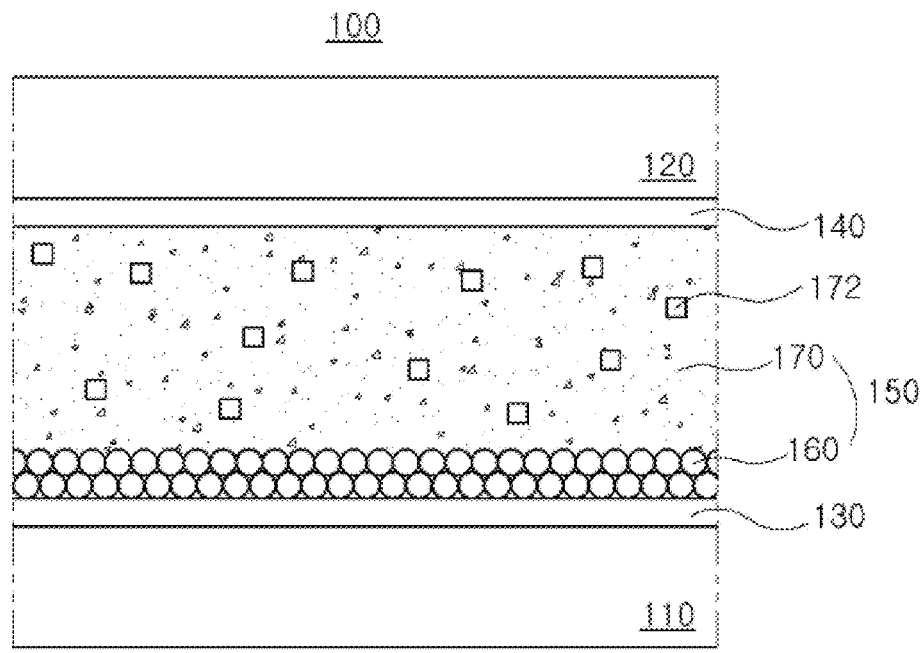
FIG. 1 is a cross-sectional diagram for schematically illustrating a light-transmittance-variable panel according to one exemplary embodiment of the present disclosure, in which a viologen compound is contained in an electrolyte.

Reference will now be made in detail to embodiments of the disclosure, examples of which are illustrated in the accompanying drawings.

[Viologen Compound]

A viologen compound according to the present disclosure has piperidine moieties linked, by an appropriate linker, to either side of a bipyridinium-salt moiety capable of exhibiting electrochromism. The viologen compound according to the present disclosure may be represented by the following Chemical Formula 1.

Chemical Formula 1

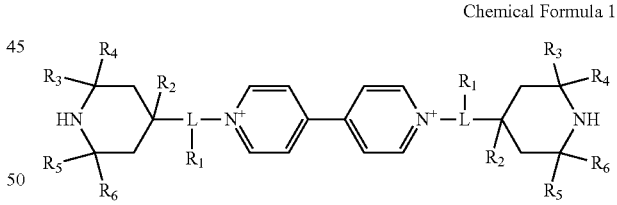

In Chemical Formula 1, $R_1$ is hydrogen, deuterium, tritium, or a linear or branched C1-C20 alkyl group, $R_2$ is hydrogen, deuterium, tritium, a C5-C30 aryl group, or a C4-C30 heteroaryl group, $R_3$ to $R_6$ are each independently hydrogen, deuterium, tritium, or a linear or branched C1-C10 alkyl group, and L is a C3-C10 alkylene group that is unsubstituted or substituted by an oxo group (=O).

For example, the heteroaryl group defined in Chemical Formula 1 is a functional group in which at least one ring-constituent carbon atom is substituted by nitrogen (N), oxygen (O), sulfur (S), phosphorus (P), etc.

In one exemplary embodiment of the present disclosure, the $R_1$ defined in Chemical Formula 1 may be a C1-C20 alkyl group and is preferably a C1-C10 alkyl group, and the $R_2$ may be a hydrogen atom or a C5-C30 aryl group (e.g., a phenyl group, a biphenyl group, a naphthalenyl group, a triphenyl group, or an anthracenyl group). In addition, each of the $R_3$ to $R_6$ in Chemical Formula 1 may independently be a C1-C10 alkyl group.

That is, the viologen compound according to the present disclosure has a structure in which a piperidine moiety is linked, by an appropriate linking group L, to each nitrogen atom included in a bipyridinium-salt moiety having an electrochromic function. The viologen compound having such a bipyridinium-salt moiety assists the function of main electrochromic particles in an electrochromic device such as a light-transmittance-variable panel. Therefore, an electrochromic device containing the viologen compound can have improved performance characteristics, particularly light-shielding characteristics.

Particularly, when either one or both of the two piperidine moieties on either side of the viologen compound according to the present disclosure is/are partly substituted by an alkyl group and the part substituted by the alkyl group is adjacent to the nitrogen atom in the same piperidine moiety, the partly substituted piperidine moiety may be able to function as a hindered amine light stabilizer (HALS). Accordingly, when the viologen compound according to the present disclosure is contained in an electrolyte or the like constituting part of an electrochromic device such as a light-transmittance-variable panel, it functions as a radical scavenger, which eliminates free radicals and stops a free-radical-generating electrolytic decomposition reaction induced by ultraviolet (UV) rays included in the irradiated light. Therefore, when contained in an electrolyte, the viologen compound according to the present disclosure can prevent a material constituting an electrochromic layer including the electrolyte from being deteriorated during light irradiation; as a result, the electrochromic layer may attain improved light-resistance characteristics.

In one exemplary embodiment of the present disclosure, the viologen compound represented by Chemical Formula 1 may specifically be represented by any one of Chemical Formula 2 to Chemical Formula 5.

Chemical Formula 2

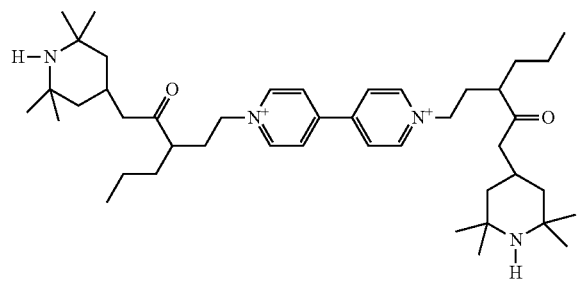

Chemical Formula 3

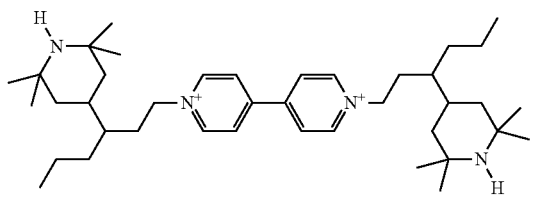

Chemical Formula 4

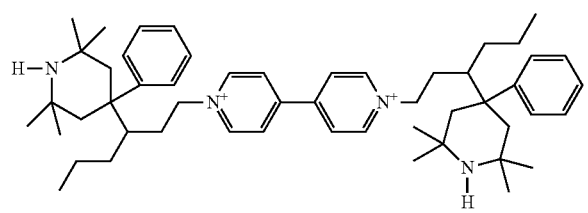

Chemical Formula 5

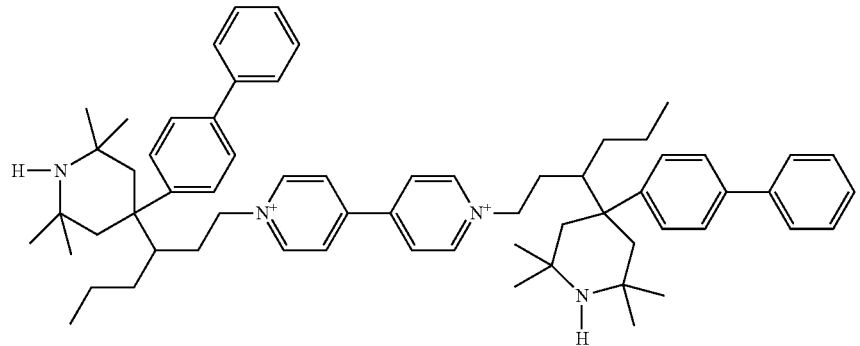

The viologen compound represented by any one of Chemical Formula 2 to Chemical Formula 5 can exhibit electrochromism. Therefore, a light-transmittance-variable panel including the viologen compound can have improved performance characteristics. In addition, since the viologen compound has a tetramethylpiperidine moiety functioning as a HALS, it can prevent the generation of free radicals caused by UV irradiation. Therefore, when the viologen compound represented by any one of Chemical Formula 2 to Chemical Formula 5 is used in an electrochromic layer, an electrochromic layer with improved light-resistance characteristics may be produced.

[Light-Transmittance-Variable Panel and Display Device]

Hereinafter, description will be provided for a light-transmittance-variable panel that includes an electrochromic layer and an electrolyte containing the viologen compound according to the present disclosure; and a display device that includes the light-transmittance-variable panel. FIG. 1 is a cross-sectional diagram for schematically illustrating a light-transmittance-variable panel according to one exemplary embodiment of the present disclosure as an electrochromic device, wherein the light-transmittance-variable panel contains the viologen compound of the present disclosure.

As illustrated in FIG. 1, a light-transmittance-variable panel 100 according to one exemplary embodiment of the present disclosure includes a first substrate 110 and a second substrate 120 facing each other; a first transparent electrode 130 provided on the first substrate 110; a second transparent electrode 140 provided on the second substrate 120; and an electrochromic layer 150 provided between the first transparent electrode 130 and second transparent electrode 140 and including an electrolyte 170 containing electrochromic particles 160 and a viologen compound 172.

Both the first substrate 110 and second substrate 120 may be made of glass or plastic. For example, both the first substrate 110 and second substrate 120 are made of a plastic material selected from the group consisting of polyethersulfones (PESs), polyacrylates (PARs), polyetherimides (PEIs), polyphenylene sulfides (PPSs), polyimides (PIs), polycarbonates (PCs), polyethylene terephthalates (PETs), polyethylene naphthalates (PENs), cellulose triacetate (TACs), and cellulose acetate propionates (CAPs).

Both the first transparent electrode 130 and second transparent electrode 140 are made of a transparent electrically conductive material. For example, both the first transparent electrode 130 and second transparent electrode 140 are made of a transparent electrically conductive material such as an indium tin oxide (ITO) or an indium zinc oxide (IZO). Since the light-transmittance-variable panel 100 according to the present embodiment of the present disclosure is required to have high light transmittance in a light-transmitting mode, it is preferable that the first transparent electrode 130 and second transparent electrode 140 be made of a transparent electrically conductive material. On the other hand, when the first transparent electrode 130 and second transparent electrode 140 are made of a low-resistance metal such as aluminum, copper, palladium, or a mixture thereof, they may be formed to have a low thickness to allow light transmission therethrough.

When necessary, the first transparent electrode 130 and second transparent electrode 140 may have a structure in which a transparent electrically conductive material such as an ITO or an IZO is deposited on a low-resistance metal such as aluminum, copper, palladium, or a mixture thereof. In this case, the low-resistance metal may be formed into a mesh structure. When transparent electrodes having a structure in which a transparent electrically conductive material is deposited on a mesh made of a low-resistance metal are used, a response rate of the electrochromic particles 160 is greatly improved; therefore, a rapid color change induced by the application of electrical power can be achieved.

The electrochromic layer 150 is provided between the first substrate 110 and second substrate 120. In other words, the electrochromic layer 150 is provided between the first transparent electrode 130 and second transparent electrode 140. In addition, the electrochromic layer 150 includes the electrolyte 170 in which the electrochromic particles 160 and viologen compound 172 are dispersed.

The electrochromic particles 160 may have a core-shell structure. For example, the electrochromic particles 160 each having a core-shell structure are dispersed in a transparent electrolytic fluid to form a dispersion, which is then applied as a coating layer or formed into a film. In another example, the electrochromic particles 160 having a core-shell structure are mixed with a transparent solid-state electrolyte (SSE) or a polymer/gel electrolyte to form a mixture, which is then applied as a coating layer or formed into a film. More detailed description of the electrochromic particles 160 will be provided hereinafter.

Figure 2:
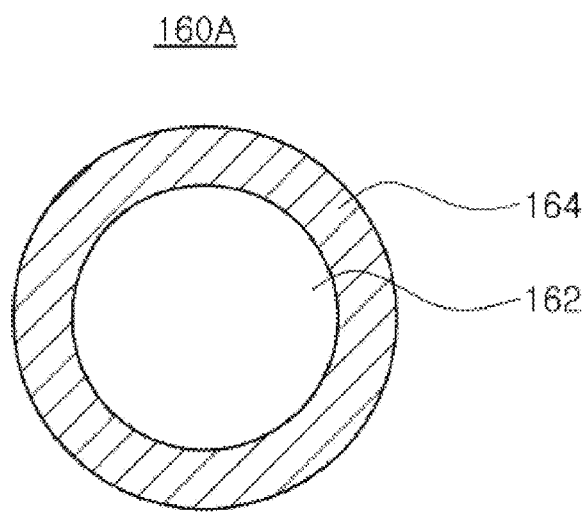
FIG. 2 schematically illustrates an electrochromic particle according to one exemplary embodiment having a single core and including a shell made of an electrochromic material.

FIG. 2 is a diagram for schematically illustrating one of electrochromic particles 160A according to one exemplary embodiment of the present disclosure, which has a single-cored core-shell structure. As illustrated in FIG. 2, each of the electrochromic particles 160A according to the one exemplary embodiment includes a core 162 and a shell 164 enclosing the core 162.

The core 162 may be made of an electrically conductive metal oxide with excellent visible light transmittance, an electrically non-conductive metal oxide having a large specific surface area, or a mixture thereof. The electrically conductive metal oxide may be a metal-oxide nanoparticle having an average diameter of, for example, 30 to 200 nm. The electrically conductive metal oxide may be selected from the group consisting of ITOs, IZOs, antimony tin oxides (ATOs), fluorine-doped tin oxides (FTOs), aluminum zinc oxides (AZOs), and combinations thereof. On the other hand, the electrically non-conductive metal oxide may be a metal-oxide nanoparticle having, for example, a specific surface area of 100 $m^2/g$ or more and an average diameter of 10 to 100 nm. The electrically non-conductive metal oxide may be selected from the group consisting of titania ($TiO_2$), silica ($SiO_2$), zinc oxide (ZnO), zirconia ($ZrO_2$), and mixtures thereof.

The material for the core 162 is not limited to those listed above, and examples thereof may further include other organic or inorganic materials exhibiting high visible light transmittance and excellent electrical conductivity, mixtures of such organic and inorganic materials; and other electrically non-conductive organic or inorganic materials with a relatively large specific surface area, and mixtures of such organic and inorganic materials.

Meanwhile, the shell 164 may be made of a material capable of changing color in response to the application of electricity. In one exemplary embodiment of the present disclosure, the shell 164 is a metal oxide such as tungsten (VI) oxide ($WO_3$), molybdenum (VI) oxide ($MoO_3$), niobium (V) oxide ($Nb_2O_5$), titania ($TiO_2$), tantalum (V) oxide ($Ta_2O_5$), nickel (IV) oxide ($NiO_2$), nickel tungsten oxide ($Ni_xW_{1-x}O_y$), iridium (VI) oxide ($IrO_3$), chromium oxide ($CrO_3$), manganese (IV) oxide ($MnO_2$), iron (IV) oxide ($FeO_2$), cobalt (IV) oxide ($CoO_2$), rhodium (IV) oxide ($RhO_2$), or vanadium (V) oxide ($V_2O_5$), whose color can be changed by an oxidation-reduction reaction.

In an alternative embodiment of the present disclosure, the shell 164 may be made of an electrochromic organic compound having a viologen structure in which two pyridinium-salt moieties are linked. When an organic compound is used as a material constituting the shell 164, a rate of response to applied electrical power may be improved; therefore, a light-transmittance-variable panel 100 with improved performance characteristics may be produced. For example, the organic electrochromic material having a viologen structure is represented by Chemical Formula 6 or Chemical Formula 7 provided below.

Chemical Formula 6

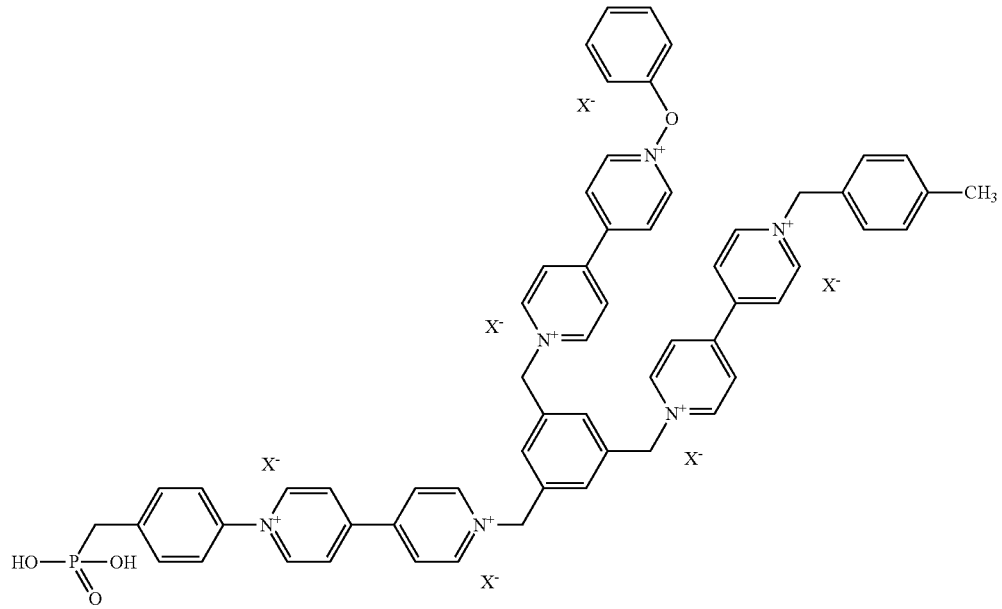

Chemical Formula 7

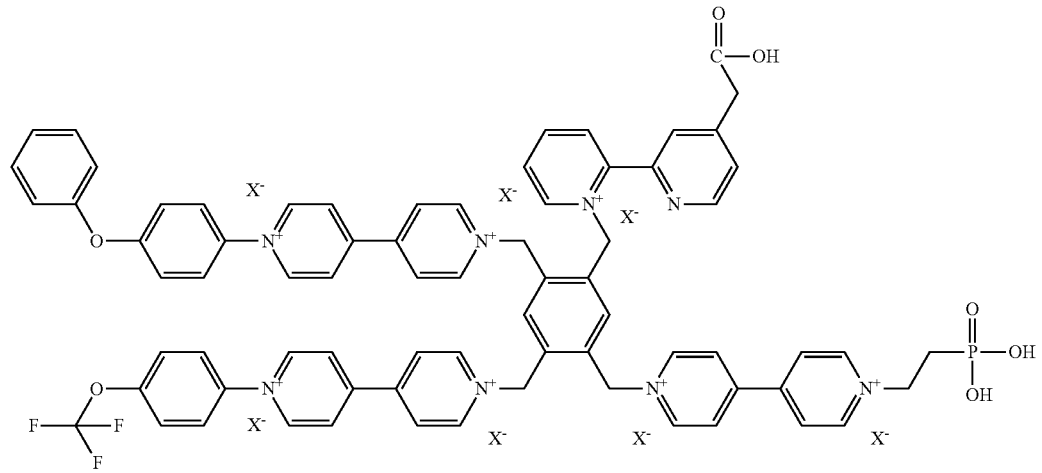

In Chemical Formula 6 and Chemical Formula 7, X is a halogen anion, $PF_6^-$, $BF_4^-$, $BH_4^-$, $ClO_4^-$, $CF_3SO_3^-$, or $(CF_3SO_2)_2N^-$.

The electrochromic material represented by Chemical Formula 6 or Chemical Formula 7 has a plurality of bipyridinium-salt moieties linked to a benzene ring, and phenyl-phenoxy moieties thereof can be engaged in stacking with the plurality of bipyridinium-salt moieties. When used to form the shell 164, the organic electrochromic material represented by Chemical Formula 6 or Chemical Formula 7 imparts excellent transparency to electrochromic particles 160, and thus the light transmittance of the electrochromic particles 160 increases when no electric field is applied. The color of the shell 164 made of an electrochromic material can be changed to black even with the application of a low drive voltage, which results in improved light-shielding efficiency.

In addition, the electrochromic particles 160A have a larger specific surface area when the core-shell structure is spherical rather than plate-like. Therefore, when the electrochromic particles 160A have a spherical core-shell structure, they may have an improved rate of response to the application of an electric field and undergo a color change even with a low drive voltage.

Figure 3:
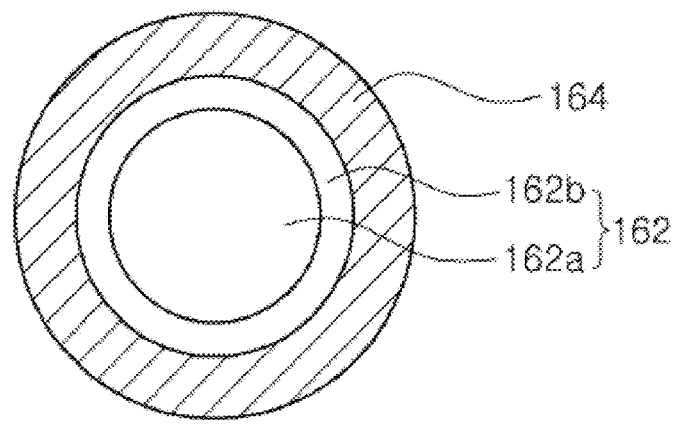
FIG. 3 schematically illustrates an electrochromic particle according to a second exemplary embodiment of the present disclosure having a double core and including a shell made of an electrochromic material.

Meanwhile, FIG. 3 is a diagram for schematically illustrating an electrochromic particle according to another exemplary embodiment of the present disclosure, which has a double-cored core-shell structure. As illustrated in FIG. 3, each of the electrochromic particles 160B according to another exemplary embodiment of the present disclosure includes a core 162 consisting of a first core 162a and a second core 162b; and a shell 164 enclosing the core 162.

For example, the first core 162a is made of an electrically conductive metal oxide exhibiting excellent visible light transmittance and satisfactory electron mobility. The first core 162a may be an electrically conductive metal oxide nanoparticle having an average diameter of, for example, 30 to 200 nm. An electrically conductive metal oxide selected from the group consisting of ITO, IZO, ATO, FTO, AZO, and combinations thereof may be used to form the first core 162a. However, the material for the first core 162a is not limited to the materials listed above, and examples thereof may further include other organic or inorganic materials exhibiting high visible light transmittance and excellent electrical conductivity, and a mixture of such an organic material and inorganic material.

The second core 162b encloses the first core 162a and is made of an electrically non-conductive metal oxide exhibiting a relatively large specific surface area and high visible light transmittance. The second core 162b may be an electrically non-conductive metal oxide nanoparticle having, for example, a specific surface area of 100 $m^2/g$ or more and an average diameter of 10 to 100 nm. An electrically non-conductive metal oxide selected from the group consisting of titanium oxide ($TiO_2$), silica ($SiO_2$), zinc oxide (ZnO), zirconia ($ZrO_2$), and combinations thereof may be used to form the second core 162b. The material for the second core 162b is not limited to those listed above, and examples thereof may further include other electrically non-conductive organic or inorganic materials with a relatively large specific surface area, and a mixture of such organic inorganic materials.

When the core 162 in each of the electrochromic particles 160B has a double-cored structure consisting of the first core 162a being electrically conductive and second core 162b having a large specific surface area and being electrically non-conductive, improvement in light transmittance and light-shielding ability is achieved and low power consumption is attained. Since the first core 162a is made of an ITO with excellent electron transfer characteristics, electron mobility towards the shell 164 in an "ON" state is increased, which facilitates color change of the shell 164.

In addition, since the second core 162b is made of $TiO_2$ or the like having high visible light transmittance, it exhibits high light transmittance in an "OFF" state. Not only that, the electrically non-conductive metal oxide constituting the second core 162b has a large specific surface area; therefore, the second core 162b is in close contact with the shell 164, which results in improved bistability of the electrochromic particles 160B. Accordingly, the electrochromic particles 160B may also be made to operate with lower power consumption. That is, because of high bistability, a light-shielded state can be maintained for a certain period of time even when the application of a voltage is interrupted, which positively affects power consumption. The shell 164 may be a metal oxide such as a tungsten oxide; or an organic compound having the viologen structure represented by Chemical Formula 6 or Chemical Formula 7.

Moreover, the electrochromic layer 150 contains, in addition to the electrochromic particles 160, an electrolyte 170 containing a viologen compound 172. The viologen compound 172 may be represented by any one of Chemical Formula 1 to Chemical Formula 5. When contained in the electrolyte 170, the viologen compound 172 improves the light-shielding characteristics and light-resistance characteristics of the electrochromic layer 150 as well as those of the electrolyte 170. The viologen compound 172 may be contained in an amount of 0.1 to 1 wt % in the electrolyte 170. When the content of the viologen compound 172 is below 0.1 wt %, improvements in light-shielding characteristics and light-resistance characteristics may not be achieved. On the other hand, when the content of the viologen compound 172 exceeds 1 wt %, an oxidation-reduction reaction is less likely to take place in the electrolyte 170.

The electrolyte 170 is, for example, an SSE. When a liquid electrolyte is used, there is a risk of the electrolytic fluid leaking to the outside. For example, a gel-type or polymer-based electrolyte containing a lithium salt dissolved therein is used as the electrolyte 170. Preferably, the electrolyte 170 is an SSE having a heat-curable or photo-curable medium and exhibiting relatively low electrical conductivity and excellent ionic conductivity.

According to one exemplary embodiment of the present disclosure, a poly(vinylidene fluoride-co-hexafluoropropylene) (PVDF-HFP), a polyacrylonitrile (PAN), poly(methyl methacrylate) (PMMA), a poly(2-acrylamido-2-methyl-1-propanesulfonic acid) (poly-AMPS), a modified polyethylene oxide (modified PEO), etc. may be used as a gel-forming polymer capable of forming a gel-type electrolyte or a polymer capable of forming a polymer-based electrolyte.

A lithium salt may be contained in the gel-type electrolyte or polymer-based electrolyte in a concentration of 0.1 to 1 mol/liter. Examples of a lithium salt that may be contained in the electrolyte include lithium bis((trifluoromethyl)sulfonyl)amide ($LiTf_2N$), lithium trifluoromethanesulfonate (LiTfO; $LiCF_3SO_3$), lithium bis(trifluoromethanesulfonyl) imide (LiTFSI), and lithium perchlorate ($LiClO_4$), but the present disclosure is not limited thereto.

The electrochromic layer 150 including the electrolyte 170 containing the electrochromic particles 160 and viologen compound 172 dispersed therein and having a thickness of, for example, 20 to 200 µm is provided on the first transparent electrode 130 or second transparent electrode 140. When the thickness of the electrochromic layer 150 is below 20 µm, a light-transmittance-variable panel 100 with poor performance characteristics may be produced. On the other hand, when the thickness of the electrochromic layer 150 exceeds 200 µm, a device with a low response rate may be produced, and blurring of adjacent pixels may occur.

Figure 4:
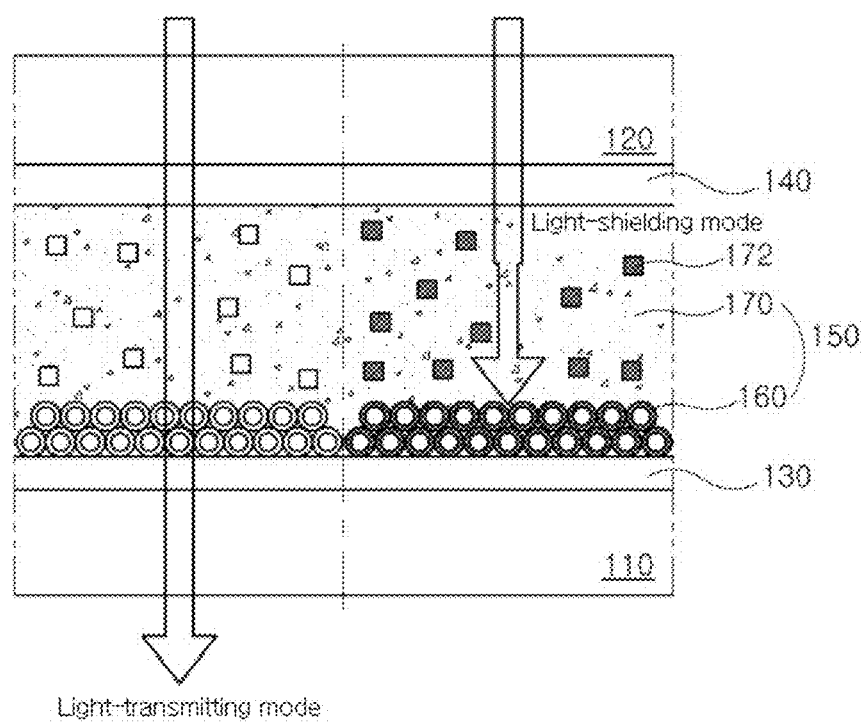
FIG. 4 is a diagram for schematically illustrating a light-shielding mode and a light-transmitting mode, each implemented with and without the application of a voltage to a light-transmittance-variable panel according to an embodiment of the present disclosure.

The light-transmittance-variable panel 100 having the above-described configuration implements a light-transmitting mode or a light-shielding mode depending on whether or not a voltage is applied. That is, since the electrochromic particles 160 and viologen compound 172 are transparent in an "OFF" state in which no voltage is applied to the first transparent electrode 130 and second transparent electrode 140, the light-transmittance-variable panel 100 can implement a light-transmitting mode by allowing light to be transmitted therethrough (see left half of FIG. 4). On the other hand, when a voltage is applied to the first transparent electrode 130 and second transparent electrode 140, the electrochromic particles 160 and viologen compound 172 undergo a color change, which allows the light-transmittance-variable panel 100 to implement a light-shielding mode in which light transmission is inhibited (see right half of FIG. 4). In this way, the light transmittance of the light-transmittance-variable panel 100 may be varied depending on whether or not a voltage is applied, and the light-transmittance-variable panel 100 may be used in a transparent display device as will be described below to produce a transparent display device with improved visibility and enhanced contrast ratio.

In particular, the viologen compound 172 represented by any one of Chemical Formula 1 to Chemical Formula 5 is contained in the electrochromic layer 150 including the electrolyte 170. Therefore, when electrical power is applied to the light-transmittance-variable panel 100, part of incident light is blocked in the electrolyte 170 by the viologen compound 172 whose color has changed to black, and the rest of the incident light is emitted to the electrochromic particles 160. This way, a light-shielding mode is implemented. In other words, the viologen compound 172 can effectively implement the light-shielding mode by assisting the electrochromic particles 160 to function as a main light-shielding material. Also, the viologen compound 172 suppresses the generation of free radicals during UV irradiation so that the electrochromic layer 150 including the electrolyte 170 is not deteriorated by UV rays. Therefore, the electrochromic layer 150 including the electrolyte 170 containing the viologen compound 172 has improved light-resistance characteristics and can maintain satisfactory performance characteristics even after a lapse of time.

Figure 5:
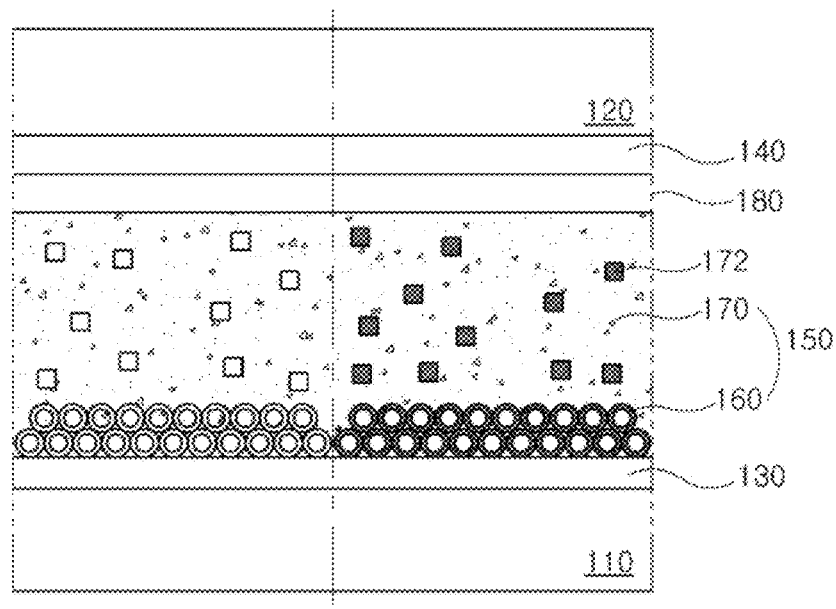
FIG. 5 is a cross-sectional diagram for schematically illustrating a light-transmittance-variable panel according to another exemplary embodiment of the present disclosure, which includes a counter electrode in addition to an electrolyte containing a viologen compound. The right and left halves of FIG. 5 illustrate a light-shielding mode and a light-transmitting mode, respectively.

Meanwhile, FIG. 5 is a cross-sectional diagram for schematically illustrating a light-transmittance-variable panel according to another exemplary embodiment of the present disclosure. As illustrated in FIG. 5, a light-transmittance-variable panel 200 according to another exemplary embodiment of the present disclosure further includes a counter electrode 180 provided between a second transparent electrode 140 and an electrochromic layer 150.

Each of a first substrate 110 and a second substrate 120 may be made of glass or a plastic material selected from the group consisting of PESs, PARs, PEIs, PPSs, PIs, PCs, PETs, PENs, TACs, and CAPs.

Both a first transparent electrode 130 and a second transparent electrode 140 are made of a transparent electrically conductive material such as an ITO and an IZO. When necessary, the first transparent electrode 130 and second transparent electrode 140 may have a structure in which a transparent electrically conductive material such as an ITO or an IZO is deposited on a low-resistance metal such as aluminum, copper, palladium, or a mixture thereof.

The electrochromic layer 150 is provided between the first transparent electrode 130 and second transparent electrode 140 and includes an electrolyte 170 in which electrochromic particles 160 and a viologen compound 172 are dispersed. The electrochromic particles 160 may have a core-shell structure, and the electrolyte 170 may be an SSE, but the present disclosure is not limited thereto.

Meanwhile, the counter electrode 180 is intended for promoting an oxidation-reduction reaction induced by an electric field in the electrochromic layer 150. That is, the counter electrode 180 promotes an oxidation-reduction reaction induced by an electric field in the electrochromic layer 150 to facilitate ion migration in the electrolyte 170 and thereby allows the electrochromic particles 160 to be reduced.

For example, the counter electrode 180 may be made of a metal oxide selected from the group consisting of cerium (IV) oxide ($CeO_2$), titania ($TiO_2$), tungsten (VI) oxide ($WO_3$), nickel (II) oxide (NiO), molybdenum (VI) oxide ($MoO_3$), vanadium (V) oxide ($V_2O_5$), and combinations thereof. In this case, the counter electrode 180 may be produced by applying a dispersion solution including the metal oxide onto the second transparent electrode 140, followed by drying and sintering of the applied solution. Alternatively, the counter electrode 180 may be deposited on the second transparent electrode 140 by a deposition method employing the metal oxide in a vaporized form, such as by chemical vapor deposition (CVD) or physical vapor deposition (PVD).

In an alternative embodiment of the present disclosure, the counter electrode 180 may be made of a material selected from the group consisting of metallocene compounds or derivatives (e.g., poly(3,4-ethylenedioxythiophene) (PEDOT) and ferrocene), diphenylamine, triphenylamine, phenothiazine-based polymers, and phenoxazine-based polymers. For example, the counter electrode 180 is an acrylic copolymer disclosed in Korean Laid-open Patent Application No. 10-2016-0055352, which has metallocene moieties and a triarylamine group. In another alternative embodiment of the present disclosure, the counter electrode 180 may be a metallocene-based polymer having a repeating unit represented by Chemical Formula 8 or Chemical Formula 9 provided below; or a metallocene-based polymer partly substituted by a vinyl group and having a repeating unit represented by Chemical Formula 10 (e.g., a vinylferrocene polymer).

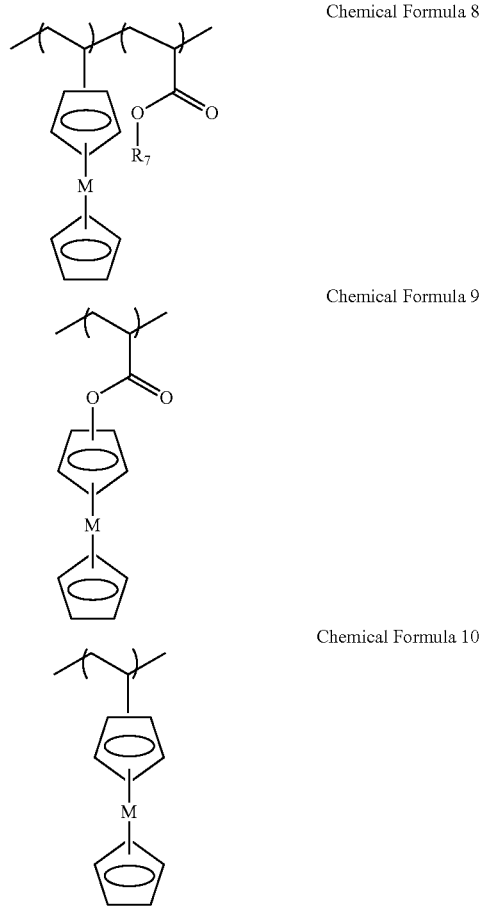

Chemical Formula 8

Chemical Formula 9

Chemical Formula 10

In Chemical Formula 8 to Chemical Formula 10, M is a transition metal selected from the group consisting of, for example, titanium (Ti), vanadium (V), chromium (Cr), manganese (Mn), iron (Fe), cobalt (Co), nickel (Ni), ruthenium (Ru), osmium (Os), and palladium (Pd). In Chemical Formula 8, $R_7$ is a C1-C10 linear or branched alkyl group.

In one exemplary embodiment of the present disclosure, the counter electrode 180 has a thickness of 200 to 800 nm. When the thickness of the counter electrode 180 is below 200 nm, the electrochromic layer 150 may have poor performance characteristics. On the other hand, when the thickness of the counter electrode 180 exceeds 800 nm, a low response rate may be attained due to increased resistance.

The electrochromic layer 150 constituting part of the light-transmittance-variable panel 200 according to a second embodiment of the present disclosure includes electrochromic particles 160; and an electrolyte 170 containing a viologen compound 172 represented by any one of Chemical Formula 1 to Chemical Formula 5. A light-shielding mode and a light-transmitting mode are implemented when the color state of the electrochromic particles 160 and viologen compound 172 changes to black with the application of electrical power and to transparent without the application of electrical power.

In particular, since the viologen compound 172 can exhibit electrochromism, it assists the electrochromic particles 160 to function as a main light-shielding material when electrical power is applied to the light-transmittance-variable panel 200. Since the colors of both the viologen compound 172 and electrochromic particles 160 change to black, the light-transmittance-variable panel 200 can have improved performance characteristics in the light-shielding mode. Also, by preventing the generation of free radicals during UV irradiation, the viologen compound 172 prevents the electrochromic layer 150 including the electrolyte 170 and electrochromic particles 160 from being deteriorated. Therefore, the electrochromic layer 150 and light-transmittance-variable panel 200 according to the present disclosure have improved light-resistance characteristics such that they can exhibit desirable performance characteristics, particularly excellent light-shielding characteristics and a high response rate, even when continuously irradiated with light.

Figure 6:
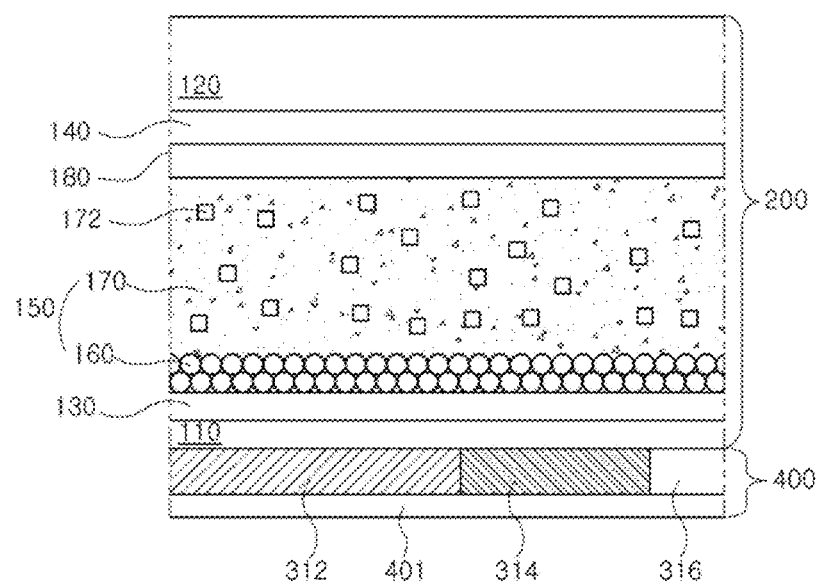
FIG. 6 is a cross-sectional diagram for schematically illustrating a display device including a light-transmittance-variable panel according to one exemplary embodiment of the present disclosure.
Figure 7:
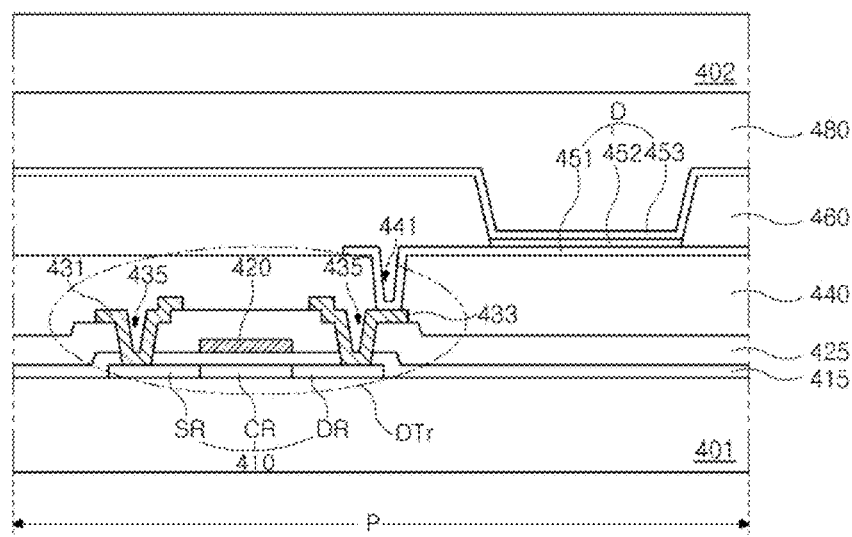
FIG. 7 is a cross-sectional diagram for schematically illustrating an organic light-emitting diode (OLED) display panel as an example of a display panel constituting part of a display device according to one exemplary embodiment of the present disclosure.

Subsequently, a display device provided with a counter electrode made of an organic/inorganic composite material according to the present disclosure will be described. FIG. 6 is a cross-sectional diagram for schematically illustrating a display device including a light-transmittance-variable panel according to one exemplary embodiment of the present disclosure, wherein the light-transmittance-variable panel 200 includes a counter electrode made of an organic/inorganic composite material according to the present disclosure. FIG. 7 is a cross-sectional diagram for schematically illustrating a display panel constituting part of a display device.

As illustrated in FIG. 6, a display device 300 includes a transparent display panel 400; and a light-transmittance-variable panel 200 provided on one side of the transparent display panel 400. The transparent display panel 400 includes a plurality of pixels, and each pixel includes a display unit 312, a driving unit 314, and a transparent unit 316. The display unit 312 is operated by a voltage or signal supplied through the driving unit 314 and displays an image. The transparent display panel 400 may be a liquid-crystal panel or a light-emitting diode panel such as an organic light-emitting diode (OLED) panel and a quantum-dot light-emitting diode panel.

The case in which the transparent display panel 400 is a light-emitting diode panel will be briefly described. Referring to FIG. 7, which is a cross-sectional diagram for schematically illustrating the display panel shown in FIG. 6, the transparent display panel 400 includes a third substrate 401 and a fourth substrate 402 facing each other, wherein a light-emitting diode D is provided as a display element between the third substrate 401 and fourth substrate 402.

Each of the third substrate 401 and fourth substrate 402 may be made of glass or plastic. For example, each of the third substrate 401 and fourth substrate 402 is made of a plastic material selected from the group consisting of PESs, PARs, PEIs, PPSs, PIs, PCs, PETs, PENs, TACs, and CAPs.

Provided on the third substrate 401 are a gate wiring and a data wiring defining a pixel region P by intersecting each other; and a power-supply wiring provided apart from and in parallel to either the gate wiring or data wiring. The display unit 312, driving unit 314, and transparent unit 316 shown in FIG. 6 are defined in each pixel region P. A switching thin-film transistor is provided in each pixel region P at the intersection of the gate wiring and data wiring.

In addition, a driving thin-film transistor DTr connected to both the switching thin-film transistor and power-supply wiring is provided. The driving thin-film transistor DTr includes a semiconductor layer 410, a gate electrode 420, a source electrode 431, and a drain electrode 433. The switching thin-film transistor may have a structure similar to that of the driving thin-film transistor DTr.

The semiconductor layer 410 includes a channel region CR; and a source region SR and a drain region DR provided on either side of the channel region CR. The semiconductor layer 410 may be made of polycrystalline silicon or oxide semiconductor. Meanwhile, a buffer layer may be provided between the semiconductor layer 410 and third substrate 401, in which case the buffer layer may be made of silica ($SiO_2$) or silicon nitride (SiNx).

Provided on the semiconductor layer 410 is a gate insulating film 415. The gate insulating film 415 may be made of an inorganic insulating material such as silica ($SiO_2$) and silicon nitride (SiNx). On the gate insulating film 415, a gate electrode 420 is formed corresponding to the channel region CR. The gate electrode 420 may be made of a low-resistance metal such as copper or aluminum.

Provided on the gate electrode 420 is an interlayer insulating film 425. The gate insulating film 415 and interlayer insulating film 425 may be provided with a semiconductor-layer contact hole 435 for exposing part of the source region SR and drain region DR, respectively, in the semiconductor layer 410. The interlayer insulating film 425 may be made of an inorganic insulating material such as silica ($SiO_2$) or silicon nitride (SiNx).

Provided on the interlayer insulating film 425 are a source electrode 431 and a drain electrode 433. The source electrode 431 and drain electrode 433 contact the source region SR and drain region DR, respectively, in the semiconductor layer 410 through a corresponding semiconductor-layer contact hole 435. The source electrode 431 and drain electrode 433 may be made of the same material as the gate electrode 420.

On the source electrode 431 and drain electrode 433, a protective layer 440 may be provided. The protective layer 440 may be made of an inorganic insulating material such as silica ($SiO_2$) or silicon nitride (SiNx); or an organic insulating material such as photo acryl. The protective layer 440 is provided with a drain contact hole 441 for exposing part of the drain electrode 433.

FIG. 7 illustrates one example of a transparent display panel 400 in which the transparent display panel 400 is provided with a driving thin-film transistor DTr including a semiconductor layer 410 made of crystalline silicon. However, in another embodiment, a driving thin-film transistor having an inverted-staggered structure in which a semiconductor layer is made of amorphous silicon may be used. Alternatively, an oxide transistor employing an oxide semiconductor may be used. Although not shown, each pixel region P is provided with a storage capacitor.

The light-emitting diode D is provided on the protective layer 440 and electrically connected to the driving thin-film transistor DTr through the drain contact hole 441. The light-emitting diode D may include a first electrode 451, a second electrode 453, and an organic light-emitting layer 452 provided between the first electrode 451 and second electrode 453.

Here, the first electrode 451 and second electrode 453 are configured to have transparency. In this regard, the first electrode 451 and second electrode 453 may be made of a transparent electrically conductive material; for example, an oxide-based transparent electrically conductive material such as ITO, IZO, GZO, or IGZO is used. In this case, one of the first electrode 451 and second electrode 453 is a positive electrode, and the other is a negative electrode. The positive electrode is made of a material with a relatively high work function, and the negative electrode is made of a material with a relatively low work function. The first electrode 451 is connected to the drain electrode 433 of the driving thin-film transistor DTr through the drain contact hole 441 and is patterned at each pixel region P. On the other hand, one integral body of the second electrode 453 is provided for entire pixel regions P of a transparent display panel 400.

Meanwhile, on the first electrode 451, a bank 460 having one opening for each pixel region P may be provided. Such a bank 460 serves to separate neighboring pixel regions P. For each pixel region P, the organic light-emitting layer 452 is provided in a ratio of one for each opening in the bank 460. The organic light-emitting layer 452 functions to emit light when holes and electrons supplied by the first electrode 451 and second electrode 453, respectively, are combined.

The organic light-emitting layer 452 may include a light-emitting material layer that substantially emits light. In order to have improved luminous efficiency, the organic light-emitting layer 452 may have a multilayer structure. For example, the organic light-emitting layer 452 includes a hole injection layer, a hole transporting layer, an electron injection layer, and an electron transporting layer in addition to the light-emitting material layer. The light-emitting diode D having the above-described configuration generates light with luminance corresponding to the intensity of a signal applied to the gate electrode 420 in the driving thin-film transistor DTr.

Meanwhile, the fourth substrate 402 is an encapsulation substrate and covers the driving thin-film transistor DTr and light-emitting diode D. A barrier layer 480 for preventing penetration of moisture, etc. may be provided between the fourth substrate 402 and light-emitting diode D.

In FIG. 7, the region provided with a driving device such as the driving thin-film transistor DTr corresponds to the driving unit 314 illustrated in FIG. 6, and the region provided with the light-emitting diode D corresponds to the display unit 312 illustrated in FIG. 6. Meanwhile, the transparent unit 316 illustrated in FIG. 6 does not include any driving device or display device therein, and light is transmitted therethrough. In addition, the display unit 312 and driving unit 314 may be overlapped with each other.

Again referring to FIG. 6, a light-transmittance-variable panel 200 includes a first substrate 110 and a second substrate 120 facing each other; a first transparent electrode 130 provided on the first substrate 110; a second transparent electrode 140 provided on the second substrate 120; a electrochromic layer 150 provided between the first substrate 110 and second substrate 120 and including electrochromic particles 160 and an electrolyte 170; and a counter electrode 180 provided between the electrochromic layer 150 and second transparent electrode 140 so as to facilitate an oxidation-reduction reaction in the electrochromic layer 150.

Each of the first substrate 110 and second substrate 120 may be formed of glass or plastic. For example, each of the first substrate 110 and second substrate 120 is made of a plastic material selected from the group consisting of PESs, PARs, PEIs, PPSs, PIs, PCs, PETs, PENs, TACs, and CAPs.

Although the first substrate 110 in the light-transmittance-variable panel 200 and the fourth substrate 402 in the transparent display panel 400 seem to have the same configuration according to FIGS. 6 and 7, the two substrates are in fact mutually different. The light-transmittance-variable panel 200 can be stacked on the transparent display panel 400 by way of attaching the first substrate 110 and fourth substrate 402 to each other. Each of the first transparent electrode 130 and second transparent electrode 140 is made of a transparent electrically conductive material.

The electrochromic layer 150 is provided between the first transparent electrode 130 and second transparent electrode 140, and includes the electrochromic particles 160 and the electrolyte 170 containing the viologen compound 172 represented by any one of Chemical Formula 1 to Chemical Formula 5. The electrochromic particles 160 may have a core-shell structure. As the electrolyte 170 capable of constituting part of the electrochromic layer 150, a gel-type or polymer-based electrolyte containing a lithium salt dissolved therein is used. Preferably, the electrolyte 170 is an SSE having a heat-curable or photo-curable medium and exhibiting relatively low electrical conductivity and excellent ionic conductivity.

Meanwhile, the counter electrode 180 promotes an oxidation-reduction reaction induced by an electric field in the electrochromic layer 150 exhibiting electrochromism to facilitate ion migration in the electrolyte 170, and thereby allows the electrochromic particles 160 to be reduced. The counter electrode 180 may be made of a material selected from the group consisting of metallocene compounds or derivatives (e.g., PEDOT and ferrocene), diphenylamine, triphenylamine, phenothiazine-based polymers, and phenoxazine-based polymers.

The light-transmittance-variable panel 200 having the above-described configuration implements a light-transmitting mode or a light-shielding mode depending on whether or not a voltage is applied. That is, when no voltage is applied to the first transparent electrode 130 and second transparent electrode 140, the transmittance-variable panel 200 allows light to be transmitted therethrough because the electrochromic particles 160 are transparent. On the other hand, when a voltage is applied to the first transparent electrode 130 and second transparent electrode 140, the electrochromic particles 160 including an electrochromic material undergo a color change, which allows the light-transmittance-variable panel 100 to block light transmission.

For example, when no voltage is applied to the first transparent electrode 130 and second transparent electrode 140, the shell 164 (see FIGS. 2 and 3) of the electrochromic particles 160 is in a transparent state; therefore, the light-transmittance-variable panel 200 implements a light-transmitting mode, and the transparent unit 316 allows light to be transmitted therethrough. However, when a voltage is applied to the first transparent electrode 130 and second transparent electrode 140, the color of the shell 164 (see FIGS. 2 and 3) of the electrochromic particles 160 changes to black; therefore, the light-transmittance-variable panel 200 implements a light-shielding mode, blocking light transmission. For this reason, the display device 300 including the light-transmittance-variable panel 200 is used as a so-called transparent display device.

As described above, the electrochromic layer 150 constituting part of the light-transmittance-variable panel 200 contains the viologen compound 172 represented by any one of Chemical Formula 1 to Chemical Formula 5. The viologen compound 172 can improve performance characteristics, i.e. light-shielding characteristics, of the light-transmittance-variable panel 200 by assisting the electrochromic particles 160 to function as a light-shielding material. In addition, the viologen compound 172 functions as a radical scavenger so that the electrochromic particles 160 and the electrochromic layer 150 including the electrolyte 170 are not deteriorated by light irradiation. Accordingly, since the electrochromic layer 150 and light-transmittance-variable panel 200 attain improved light-resistance characteristics accordingly, the light-transmittance-variable panel 200 and display device 300 exhibiting excellent performance characteristics and high response rate can be attained.

Hereinafter, the present disclosure will be described in greater detail with reference to exemplary embodiments, but the present disclosure is not limited to the technical concept described in the following embodiments.

Synthesis Example 1: Synthesis of Viologen Compound

Figure 8:
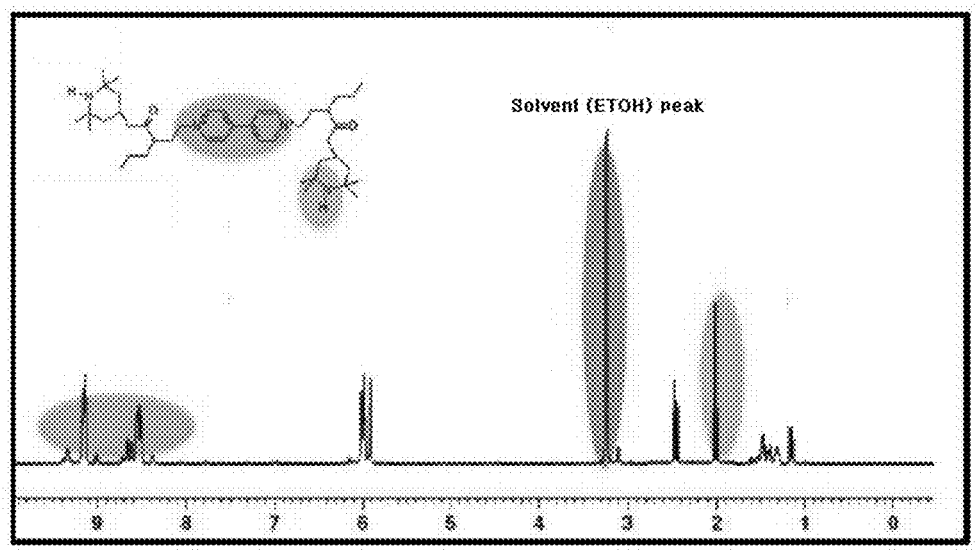
FIG. 8 shows the NMR analysis results of the viologen compound synthesized according to Synthesis Example 1.

A viologen compound represented by Chemical Formula 2 was synthesized by the following method. 15.6 g (0.1 mol) of bipyridine and 33 g (0.2 mol) of bromoethylphosphonate were added, in a nitrogen atmosphere, to a three-necked flask containing a solution including methanol and water mixed in a ratio of 50:50, and the substances were refluxed at 80° C. for 12 hours. After intermediate target compounds were identified by thin-layer chromatography (TLC), 42 g (0.2 mol) of (2,2,6,6-tetramethylpiperidine-4-yl)acetic acid hydrochloride was added, and the mixture was stirred for 70° C. for 72 hours, which was then subjected to TLC for purification. FIG. 8 shows the NMR analysis results of the viologen compound synthesized according to Synthesis Example 1.

Synthesis Example 2: Synthesis of Viologen Compound

Figure 9:
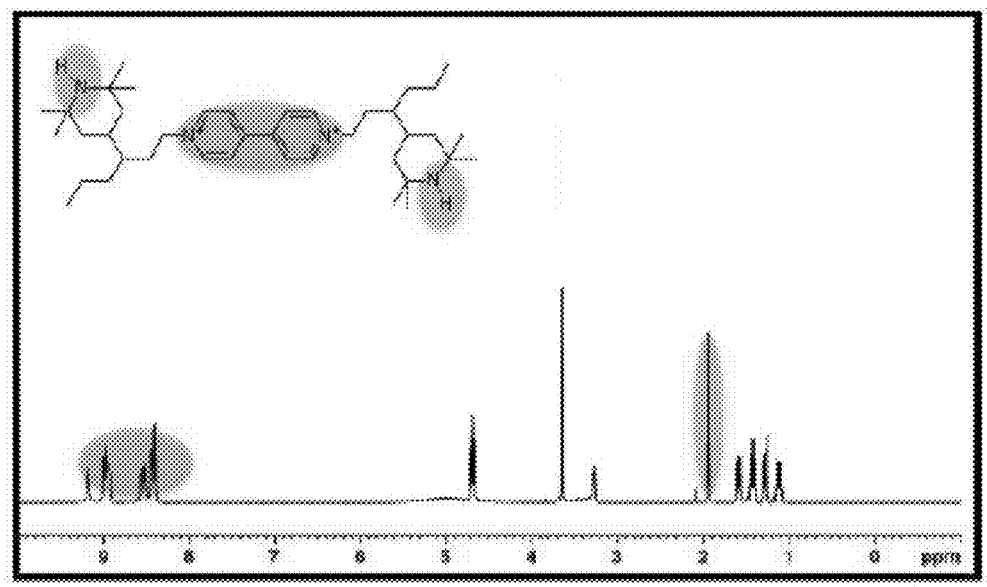
FIG. 9 shows the NMR analysis results of the viologen compound synthesized according to Synthesis Example 2.

A viologen compound represented by Chemical Formula 3 was synthesized by repeating the processes described in Synthesis Example 1 except that (2,2,6,6-tetramethylpiperidine-4-yl)methanol was used instead of the (2,2,6,6-tetramethylpiperidine-4-yl)acetic acid hydrochloride used in Synthesis Example 1. FIG. 9 shows the NMR analysis results of the viologen compound synthesized according to Synthesis Example 2.

Synthesis Example 3: Synthesis of Viologen Compound

Figure 10:
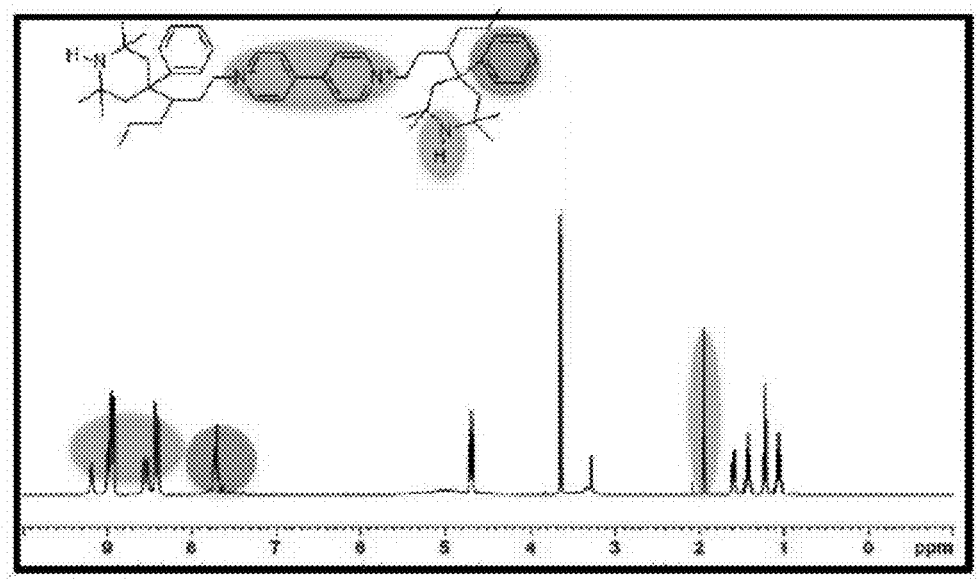
FIG. 10 shows the NMR analysis results of the viologen compound synthesized according to Synthesis Example 3.

A viologen compound represented by Chemical Formula 4 was synthesized by repeating the processes described in Synthesis Example 1 except that 2,2,6,6-tetramethyl-4-phenyl-4-piperidine was used instead of the (2,2,6,6-tetramethylpiperidine-4-yl)acetic acid hydrochloride used in Synthesis Example 1. FIG. 10 shows the NMR analysis results of the viologen compound synthesized according to Synthesis Example 3.

Synthesis Example 4: Synthesis of Viologen Compound

Figure 11:
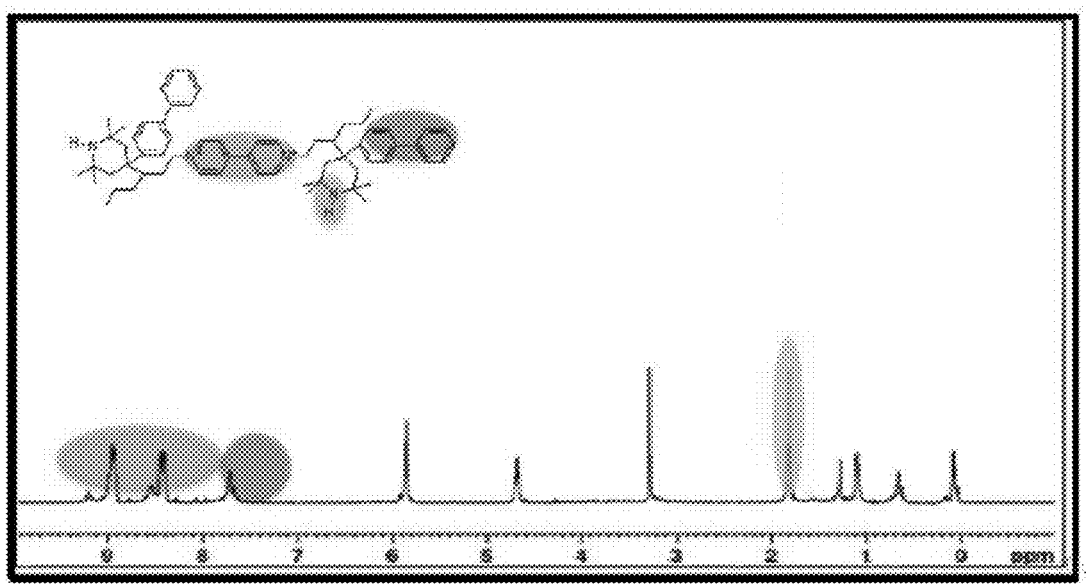
FIG. 11 shows the NMR analysis results of the viologen compound synthesized according to Synthesis Example 4.

A viologen compound represented by Chemical Formula 5 was synthesized by repeating the processes described in Synthesis Example 1 except that 4-[1,1-biphenyl]4-2,2,6,6-tetramethyl-4-piperidine was used instead of the (2,2,6,6-tetramethylpiperidine-4-yl)acetic acid hydrochloride used in Synthesis Example 1. FIG. 11 shows the NMR analysis results of the viologen compound synthesized according to Synthesis Example 4.

Example 1: Production of Unit Cell for Light-Transmittance-Variable Panel (1) Synthesis of Electrochromic Particles The synthesis of an electrochromic material represented by Chemical Formula 7, wherein the X is a bis((trifluoromethyl)sulfonyl)imide anion (($CF_3SO_2)_2N^-$), as a material constituting a shell of electrochromic particles was performed as follows. 15.6 g (0.1 mol) of bipyridine and 24.5 g of bromoethylphosphonate (0.1 mol) were added, in a nitrogen atmosphere, to a three-necked flask containing a solution including methanol and water mixed in a ratio of 50:50, and the substances were refluxed at 80° C. for 12 hours. Then, solvents were removed by distillation, and the remaining substances were purified to obtain a white solid. 40.0 g of the white solid obtained as such and 35.6 g (0.1 mol) of 1,3,5-tribromobenzene were added to a solvent prepared by mixing ethanol and toluene in a ratio of 80:20, and then the mixture was allowed to react for three days to obtain a pale-yellow substance.

70 g of the pale-yellow substance obtained as such was added to 7.1 g of 3-oxo-3-(4-phenoxyphenyl)propionic acid methyl ester (0.05 mol), 5.2 g of 1-bromo-3-(trifluoromethoxy)benzene, 31.2 g (0.2 mol) of bipyridine, and 300 g of methanol. Then, the mixture was allowed to react at 80° C. for 12 hours and primarily treated with an aqueous solution of HCl (38 wt %), from which impurities other than a target compound were removed through recrystallization to obtain an ivory-colored compound. Afterwards, the compound was added to a 1 L flask containing 1-ethyl-3-methylimidazolium bis(trifluoromethylsulfonyl)imide, and the substances were subjected to ion exchange followed by recrystallization.

2.0 g of the above-described material constituting a shell of electrochromic particles was dissolved in 20 g of methanol, and the substances were stirred at 50° C. for three hours using ultrasonic waves to obtain a transparent solution. In the meantime, 50 g of an ITO powder (primary particle size>15 nm; Solvay S.A.), 0.5 g of 2,4-pentanedione, and 0.05 g of a non-aqueous organic binder (DISPERBYK-160; BYK Additives & Instruments) were added to a 250 mL wide-mouthed bottle containing 120 g of isopropyl alcohol, and the mixture was stirred for one hour. After adding 50 g of the above-described transparent solution and 200 g of 0.1 mm zirconia beads to the above-described mixture and sealing the container, the substances were dispersed for 24 hours using a ball mill operated at a speed of 600 rpm to prepare a solution containing electrochromic particles (i.e., electrochromic-particle dispersion solution) in the form of ECP dispersion solution.

(2) Production of Electrochromic Electrolyte

A solid-state electrolyte containing the viologen compound of Synthesis Example 1 was produced as follows. 50 g of a 1:1 mixture of propylene carbonate and ethylene carbonate was added to a three-necked flask in a nitrogen atmosphere, to which 1M lithium bis(trifluoromethanesulfonyl)imide was added. After stirring the substances for 24 hours, 20 g of urethane acrylate and 0.1 g of Igacure® 184 (BASF SE) were added to the substances, and the mixture was stirred for 24 hours at room temperature to produce an electrolyte. Subsequently, 0.5 g of the viologen compound of Synthesis Example 1 was added to the electrolyte, and stirring was performed at 60° C. for five hours to produce an electrochromic electrolyte.

(3) Fabrication of Light-Transmittance-Variable Panel

A light-transmittance-variable panel was fabricated using the above-described ECP dispersion solution and electrochromic electrolyte.

A counter electrode was produced as follows. 30 g of vinylferrocene and 300 g of chlorobenzene were added to a flask equipped with a stirrer, and stirring was performed to dissolve vinylferrocene in chlorobenzene. After raising a temperature of the solution to 60° C., an initiator for radical polymerization was added to the solution at a rate of 0.05 g/min. As a result of 23 hours of reaction, a vinylferrocene polymer having a molecular weight of 8000 was obtained. The polymer synthesized as such was dissolved in dichlorobenzene, and the polymer solution was applied onto a substrate by spin coating at 1000 rpm to produce the counter electrode.

Subsequently, the ECP dispersion solution prepared earlier was applied, to a final thickness of 4 μm, onto an ITO glass film having a sheet resistance of 40 Ω/sq and then dried at 80° C. for 20 minutes to produce an electrochromic particle layer. Then, the electrochromic electrolyte produced earlier was applied onto the electrochromic particle layer such that the newly applied layer had a thickness of 100 μm after drying and curing. The newly applied layer was then cured by UV irradiation with the intensity of 0.1 J/cm$^2$ to produce a solid-state electrolyte layer based on the electrochromic electrolyte produced earlier and capable of exhibiting electrochromism.

Subsequently, the ITO glass provided with the electrochromic particle layer and solid-state electrolyte layer thereon was bonded at a temperature of 40° C. to the substrate (double-sided ITO glass) having a sheet resistance of 40 Ω/sq and provided with the counter electrode to produce a unit cell for a light-transmittance-variable panel having an active region of a size of 100 mm×100 mm.

Example 2: Production of Unit Cell for Light-Transmittance-Variable Panel

A unit cell for a light-transmittance-variable panel was produced by repeating the processes described in Example 1 except that the viologen compound synthesized according to Synthesis Example 2 was used instead of the viologen compound synthesized according to Synthesis Example 1 to produce an electrochromic electrolyte layer.

Example 3: Production of Unit Cell for Light-Transmittance-Variable Panel

A unit cell for a light-transmittance-variable panel was produced by repeating the processes described in Example 1 except that the viologen compound synthesized according to Synthesis Example 3 was used instead of the viologen compound synthesized according to Synthesis Example 1 to produce an electrochromic electrolyte layer.

Example 4: Production of Unit Cell for Light-Transmittance-Variable Panel

A unit cell for a light-transmittance-variable panel was produced by repeating the processes described in Example 1 except that the viologen compound synthesized according to Synthesis Example 4 was used instead of the viologen compound synthesized according to Synthesis Example 1 to produce an electrochromic electrolyte layer.

Comparative Example 1: Production of Unit Cell for Light-Transmittance-Variable Panel A unit cell for a light-transmittance-variable panel was produced by repeating the processes described in Example 1 except that an electrolyte layer including no viologen compound was used.

Comparative Example 2: Production of Unit Cell for Light-Transmittance-Variable Panel A unit cell for a light-transmittance-variable panel was produced by repeating the processes described in Example 1 except that a tungsten oxide was used to form electrochromic particles and a nickel oxide was used to form a layer of a counter electrode.

Experimental Example 1: Evaluation of Performance Characteristics of Light-Transmittance-Variable Panel The performance characteristics of the light-transmittance-variable panels produced according to Examples 1 to 4 and Comparative Examples 1 and 2 were evaluated using a spectrophotometer (DMS 803; Konica Minolta, Inc.). The results of the performance evaluation according to Experimental Example 1 are shown in Table 1 below. As shown in Table 1, the light-transmittance-variable panels including an electrolyte containing a viologen compound synthesized by the method of the present disclosure have excellent light-shielding characteristics in the "ON" mode.

TABLE 1

Performance characteristics of light-transmittance-variable panels

| | Transmittance (Light-transmitting ("OFF") mode) | Transmittance (Light-shielding ("ON") mode) | Response rate ($T_{90}$) | Drive voltage (V) |
|---|---|---|---|---|
| Example 1 | 75% | 0.18% | ~10 sec | 1.0 |
| Example 2 | 75% | 0.2% | ~10 sec | 1.0 |
| Example 3 | 75% | 0.2% | ~10 sec | 1.0 |
| Example 4 | 75% | 0.2% | ~10 sec | 1.0 |
| Comparative Example 1 | 75% | 1.0% | ~10 sec | 1.0 |
| Comparative Example 2 | 65% | 20% | ~90 sec | 2.2 |

Experimental Example 2: Evaluation of Light-Resistance Characteristics of Light-Transmittance-Variable Panel The light-resistance characteristics of the light-transmittance-variable panels produced according to Example 1 and Comparative Example 1 were evaluated using a solar simulator (Atlas Material Testing Solutions). The optical characteristics of each unit cell as a function of a solar exposure time were evaluated. The change in light transmittance in the light-transmitting mode and light-shielding mode was evaluated as a function of elapsed time, wherein the elapsed time was measured from the moment when the light transmittance in the light-shielding mode reached 1%. The light-transmittance-variable panel produced according to Comparative Example 1 had an initial light transmittance in the light-shielding mode of 1%, and the light-transmittance-variable panel produced according to Example 1 had an light transmittance in the light-shielding mode of 1% 10 days after the initiation of the light-shielding mode. The unit cell of the light-transmittance-variable panel produced according to Comparative Example 1 was exposed to sunlight immediately after production, and the unit cell of the light-transmittance-variable panel produced according to Example 1 was exposed to sunlight from 10 days after production. The evaluation results are shown in Table 2 below. In Table 2, the "exposure time" refers to the period of time, measured from the moment when the light transmittance in the light-shielding mode reached 1%, during which the unit cell of each light-transmittance-variable panel was exposed to sunlight generated by the solar simulator. As shown in Table 2, the light-transmittance-variable panel of the present disclosure, in which the electrolyte thereof contains the viologen compound synthesized according to the present disclosure, had excellent light-resistance characteristics by maintaining and not losing the original light-shielding characteristics even when exposed to sunlight for an extended period of time. In contrast, the light-shielding characteristics of the light-transmittance-variable panel of a comparative example, in which the electrolyte thereof did not contain a viologen compound, was rapidly deteriorated with prolonged exposure to sunlight.

TABLE 2

Performance characteristics of light-transmittance-variable panel as function of solar exposure time
Transmittance (light-transmitting mode/light-shielding mode)

| Exposure time | 1 day | 10 days | 20 days | 30 days |
|---|---|---|---|---|
| Example 1 | 75%/1% | 75%/1.2% | 75%/1.6% | 75%/1.9% |
| Comparative Example 1 | 75%/1% | 75%/3% | 75%/7% | 75%/18% |

The viologen compound according to the present disclosure has two piperidine moieties linked to either side of a bipyridinium salt by an appropriate linker. The viologen compound can exhibit electrochromism by going through an oxidation-reduction reaction affected by whether or not electrical power is applied, and has excellent light-resistance characteristics.

Therefore, when contained in an electrolyte used in an electrochromic device such as a light-transmittance-variable panel, the viologen compound can further improve light-shielding characteristics by assisting the main electrochromic particles. Also, when contained in an electrolyte, the viologen compound can prevent the electrolyte from deteriorating from being continuously irradiated with light and thereby maintains a satisfactory level of performance characteristics, particularly light-shielding characteristics, of the electrochromic device.

In addition, when an electrochromic particle consisting of a core and a shell is used as a main electrochromic material, satisfactory light-shielding efficiency can be achieved. Also, since the shell of each electrochromic particle is made of an organic material, an improved response rate can be attained, and a rapid color change can be achieved accordingly.

Moreover, the light-transmittance-variable panel according to the present disclosure includes a solid-state electrolyte (SSE) and thus can be formed into a film-type panel. Use of an SSE can prevent the problem of fluid leakage found in conventional light-transmittance-variable panels including a liquid electrolyte and can enable the production of thin light-transmittance-variable panels.

Not only that, the display device including the light-transmittance-variable panel according to the present disclosure exhibits improved visibility and contrast ratio due to the excellent light transmittance and excellent light-shielding characteristics thereof.

Although the present disclosure has been described with reference to exemplary embodiments of the present disclosure, the present disclosure is not limited to the technical concept described in the embodiments and may have various modifications and alterations made by those skilled in the art. It is evident, however, by the appended claims that all such modifications and alterations are covered within the scope of the present disclosure.

What is claimed is:

1. A viologen compound represented by Chemical Formula 1:

Chemical Formula 1

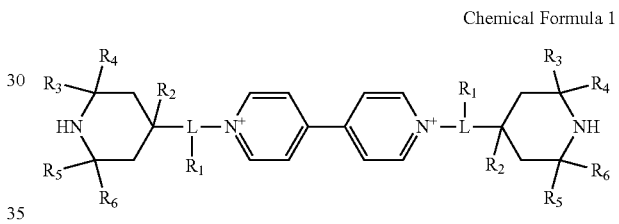

wherein $R_1$ is hydrogen, deuterium, tritium, a linear C1-C20 alkyl group, or a branched C1-C20 alkyl group;

$R_2$ is hydrogen, deuterium, tritium, a C5-C30 aryl group, or a C4-C30 heteroaryl group;

$R_3$ to $R_6$ are each independently hydrogen, deuterium, tritium, a linear C1-C10 alkyl group, or a branched C1-C10 alkyl group; and L is a C3-C10 alkylene group that is unsubstituted by an oxo group (=O) or substituted by an oxo group (=O).

2. The viologen compound according to claim 1, represented by any one of Chemical Formula 2 to Chemical Formula 5:

Chemical Formula 2

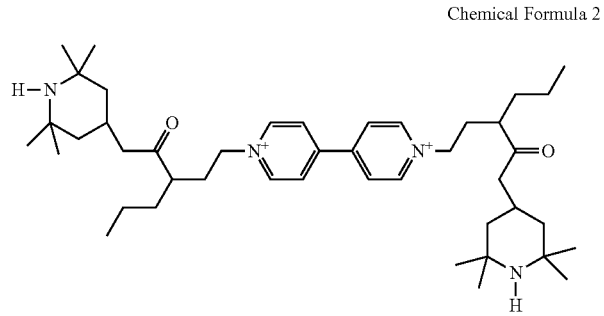

Chemical Formula 3

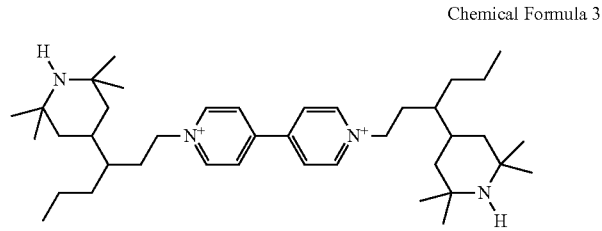

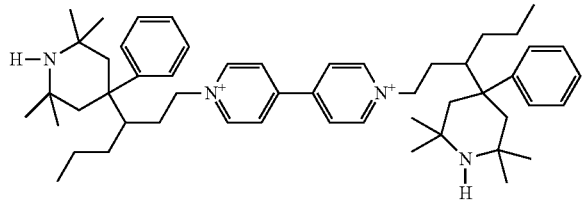

Chemical Formula 4

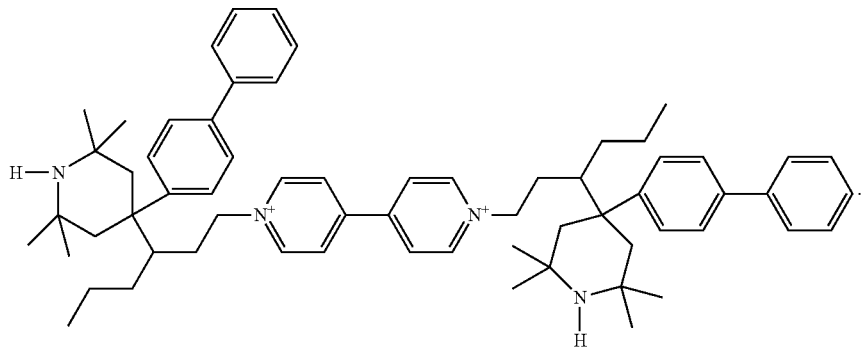

Chemical Formula 5

3. An electrolyte comprising a viologen compound represented by Chemical Formula 1:

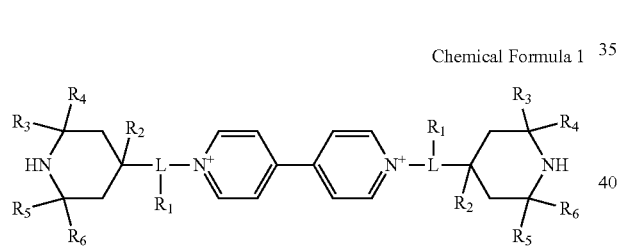

Chemical Formula 1 wherein $R_1$ is hydrogen, deuterium, tritium, a linear C1-C20 alkyl group or a branched C1-C20 alkyl group;

$R_2$ is hydrogen, deuterium, tritium, a C5-C30 aryl group, or a C4-C30 heteroaryl group;

$R_3$ to $R_6$ are each independently hydrogen, deuterium, tritium, a linear C1-C10 alkyl group, or a branched C1-C10 alkyl group; and L is a C3-C10 alkylene group that is unsubstituted or substituted by an oxo group (=O).

4. The electrolyte according to claim 3, wherein the viologen compound is included in an amount of 0.1 to 1 wt % in the electrolyte.

5. A light-transmittance-variable panel comprising:

a first substrate and a second substrate facing each other;

a first transparent electrode disposed on the first substrate;

a second transparent electrode disposed on the second substrate; and an electrochromic layer between the first transparent electrode and the second transparent electrode and containing a viologen compound represented by Chemical Formula 1:

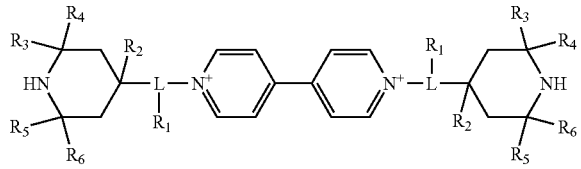

Chemical Formula 1 wherein $R_1$ is hydrogen, deuterium, tritium, a linear C1-C20 alkyl group, or a branched C1-C20 alkyl group;

$R_2$ is hydrogen, deuterium, tritium, a C5-C30 aryl group, or a C4-C30 heteroaryl group;

$R_3$ to $R_6$ are each independently hydrogen, deuterium, tritium, a linear C1-C10 alkyl group, or branched C1-C10 alkyl group; and L is a C3-C10 alkylene group that is unsubstituted by an oxo group (=O) or substituted by an oxo group (=O).

6. The light-transmittance-variable panel according to claim 5, wherein the electrochromic layer includes the viologen compound, electrochromic particles, and an electrolyte.

7. The light-transmittance-variable panel according to claim 6, wherein each of the electrochromic particles includes a core and a shell.

8. The light-transmittance-variable panel according to claim 7, wherein the shell includes a bipyridinium salt represented by Chemical Formula 6 or Chemical Formula 7:

Chemical Formula 6

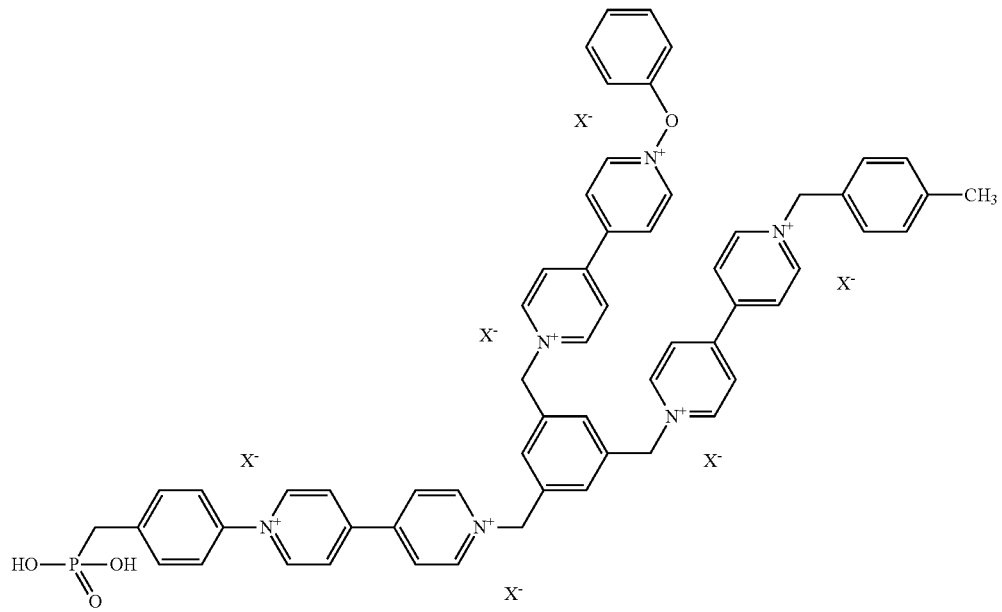

Chemical Formula 7

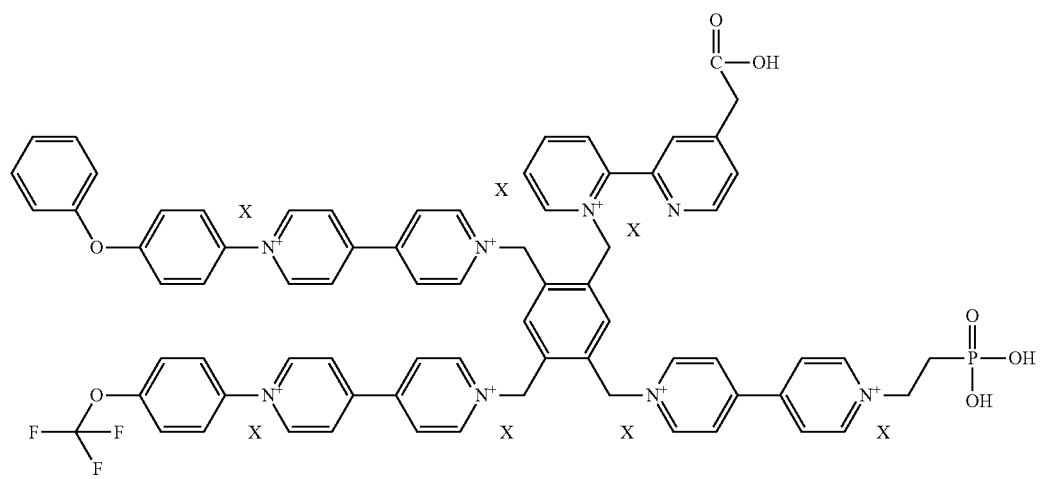

wherein, in Chemical Formula 6 and Chemical Formula 7,
X is a halogen anion, $PF_6^-$, $BF_4^-$, $BH_4^-$, $ClO_4^-$, $CF_3SO_3^-$, or $(CF_3SO_2)_2N^-$.

9. The light-transmittance-variable panel according to claim 5, further comprising a counter electrode between the second transparent electrode and the electrochromic layer, wherein said counter electrode promotes an oxidation-reduction reaction in the electrochromic layer.

10. The light-transmittance-variable panel according to claim 9, wherein the counter electrode is composed of a metallocene-based polymer having a repeating unit represented by any one of Chemical Formula 8 to Chemical Formula 10:

Chemical Formula 8

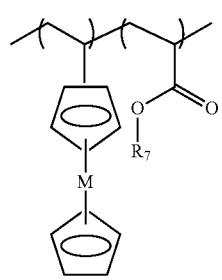

-continued

Chemical Formula 9

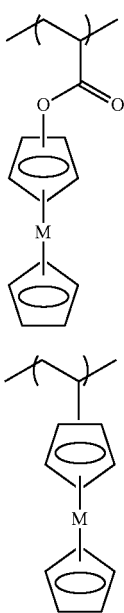

Chemical Formula 10

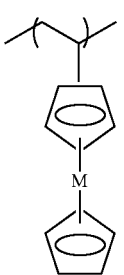

wherein, in Chemical Formula 8 to Chemical Formula 10:
M is selected from the group consisting of titanium (Ti), vanadium (V), chromium (Cr), manganese (Mn), iron (Fe), cobalt (Co), nickel (Ni), ruthenium (Ru), osmium (Os), and palladium (Pd); and
$R_7$ in Chemical Formula 8 is a C1-C10 linear alkyl group or a C1-C10 branched alkyl group.

11. A display device comprising:
a light-transmittance-variable panel including:
  a first substrate and a second substrate facing each other;
  a first transparent electrode disposed on the first substrate;
  a second transparent electrode disposed on the second substrate; and
  an electrochromic layer between the first transparent electrode and the second transparent electrode and containing a viologen compound represented by Chemical Formula 1:

Chemical Formula 1

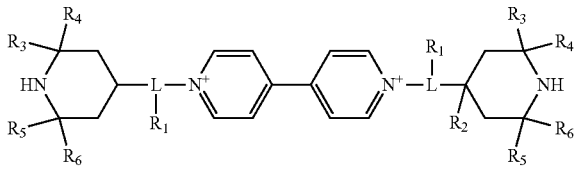

wherein $R_1$ is hydrogen, deuterium, tritium, or a linear C1-C20 alkyl group or a branched C1-C20 alkyl group;
$R_2$ is hydrogen, deuterium, tritium, a C5-C30 aryl group, or a C4-C30 heteroaryl group;
$R_3$ to $R_6$ are each independently hydrogen, deuterium, tritium, a linear C1-C10 alkyl group, or a branched C1-C10 alkyl group; and
L is a C3-C10 alkylene group that is unsubstituted by an oxo group (=O) or substituted by an oxo group (=O); and
a display panel on one side of the light-transmittance-variable panel and including a plurality of display units and a plurality of transparent units.

* * * * *